United States Patent
Hui et al.

(10) Patent No.: US 10,224,751 B2
(45) Date of Patent: Mar. 5, 2019

(54) METHODS FOR PARAMETER IDENTIFICATION, LOAD MONITORING AND OUTPUT POWER CONTROL IN WIRELESS POWER TRANSFER SYSTEMS

(71) Applicant: THE UNIVERSITY OF HONG KONG, Hong Kong (CN)

(72) Inventors: Shu Yuen Hui, Hong Kong (CN); Deyan Lin, Hong Kong (CN); Jian Yin, Hong Kong (CN); Chi Kwan Lee, Hong Kong (CN)

(73) Assignee: THE UNIVERSITY OF HONG KONG, Hong Kong (CN)

( * ) Notice: Subject to any disclaimer, the term of this patent is extended or adjusted under 35 U.S.C. 154(b) by 69 days.

(21) Appl. No.: 14/910,560

(22) PCT Filed: Aug. 6, 2014

(86) PCT No.: PCT/CN2014/083775
§ 371 (c)(1),
(2) Date: Feb. 5, 2016

(87) PCT Pub. No.: WO2015/018334
PCT Pub. Date: Feb. 12, 2015

(65) Prior Publication Data
US 2016/0181824 A1    Jun. 23, 2016

Related U.S. Application Data

(60) Provisional application No. 61/862,627, filed on Aug. 6, 2013.

(51) Int. Cl.
*H02J 50/12*      (2016.01)
*H02J 50/40*      (2016.01)
(Continued)

(52) U.S. Cl.
CPC ............. *H02J 50/12* (2016.02); *B60L 11/182* (2013.01); *G01N 27/02* (2013.01); *G01R 21/133* (2013.01);
(Continued)

(58) Field of Classification Search
CPC .......... H02M 3/07; H02J 50/50; B60L 11/182
See application file for complete search history.

(56) References Cited

U.S. PATENT DOCUMENTS

| 1,119,732 A | 12/1914 | Tesla |
| 7,576,514 B2 | 8/2009 | Hui |

(Continued)

FOREIGN PATENT DOCUMENTS

| CN | 102611210 A | 7/2012 |
| CN | 103683527 A | 3/2014 |

(Continued)

OTHER PUBLICATIONS

Zhong, et.al., "General Analysis on the Use of Tesla's Resonators in Domino Forms for Wireless Power Transfer," Jan. 2013, IEEE Transaction on industrial electronics, vol. 60, No. 1, pp. 261-270.*
Sample, "Enabling Seamless Wireless Power Delivery in Dynamic Environments," Jun. 2013, Proceeding of the IEEE, vol. 101, No. 6, pp. 1343-1358.*
International Search Report dated Nov. 19, 2014 in International Application No. PCT/CN2014/083775.
(Continued)

*Primary Examiner* — Thienvu Tran
*Assistant Examiner* — Pinping Sun
(74) *Attorney, Agent, or Firm* — Saliwanchik, Lloyd & Eisenschenk

(57) ABSTRACT

A method for identifying impedance related parameters in a wireless power transfer (WPT) system including n coils is disclosed. Said method includes determining optimum values of the impedance related parameters based on a set of measured input impedance by applying an evolutionary algorithm to solve optimum solutions. Wherein the set of measured input impedance includes an input impedance vector $\vec{Z}=(Z_1, Z_2, \ldots, Z_{m-1}, Z_m)$, each input impedance in
(Continued)

the vector ($Z_k$) measured at different frequencies $f_k$, (k=1, 2, ... m); and the impedance related parameters includes $d_{ll-1}$ representing a distance between the l-th coil and the l+1 coil (l=1, 2, ... n−1) and $C_i$ representing a capacitance of the capacitor connected to the i-th coil (i=1, 2, ... n).

19 Claims, 7 Drawing Sheets

(51) Int. Cl.
  *G01N 27/02* (2006.01)
  *G01R 21/133* (2006.01)
  *H02J 5/00* (2016.01)
  *H02J 7/02* (2016.01)
  *B60L 11/18* (2006.01)
  *H02J 50/50* (2016.01)

(52) U.S. Cl.
  CPC .............. *H02J 5/005* (2013.01); *H02J 7/025* (2013.01); *H02J 50/40* (2016.02); *H02J 50/50* (2016.02)

(56) References Cited

U.S. PATENT DOCUMENTS

| | | | |
|---|---|---|---|
| 8,334,620 B2* | 12/2012 | Park | G01R 27/02 307/104 |
| 8,643,326 B2* | 2/2014 | Campanella | H01Q 7/00 320/108 |
| 9,065,302 B2* | 6/2015 | Kamata | H02J 7/025 |
| 2008/0211320 A1* | 9/2008 | Cook | H01Q 7/005 307/149 |
| 2009/0307636 A1* | 12/2009 | Cases | G06F 17/505 716/132 |
| 2011/0065398 A1 | 3/2011 | Liu et al. | |
| 2012/0153739 A1 | 6/2012 | Cooper et al. | |
| 2012/0306265 A1* | 12/2012 | Yamamoto | B60L 5/005 307/9.1 |
| 2013/0069440 A1 | 3/2013 | Marukame et al. | |
| 2013/0082535 A1 | 4/2013 | Miyauchi et al. | |
| 2013/0154386 A1* | 6/2013 | Bae | H02J 5/005 307/104 |
| 2014/0028112 A1* | 1/2014 | Hui | H01F 38/14 307/104 |
| 2014/0084688 A1* | 3/2014 | Tzanidis | H01F 38/14 307/42 |
| 2014/0084701 A1* | 3/2014 | Bae | H02J 5/005 307/104 |
| 2014/0175895 A1* | 6/2014 | Ishi | H02J 17/00 307/104 |
| 2015/0280444 A1* | 10/2015 | Smith | H02J 17/00 307/104 |

FOREIGN PATENT DOCUMENTS

| | | |
|---|---|---|
| EP | 2 216 870 A2 | 8/2010 |
| EP | 2 720 349 A1 | 4/2014 |
| EP | 2 722 967 A1 | 4/2014 |
| KR | 101235356 B1 | 2/2013 |
| WO | WO-2012/169584 A1 | 12/2012 |
| WO | WO-2012/172899 A1 | 12/2012 |
| WO | WO-2013/048034 A1 | 4/2013 |
| WO | WO-2014/115997 A1 | 7/2014 |

OTHER PUBLICATIONS

Schuder, J.C. et al., High-level electromagnetic energy transfer through a closed chest wall, IRE Int. Conv. Rec., 1961, 9(9):119-126.
Ko, Wen H. et al., Design of radio-frequency powered coils for implant instruments, Medical & Biological Engineering & Computing, Nov. 1977, 15(6):634-640, Kluwer Academic Publishers.
Hurley, William G. et al., Induction Heating of Circular Ferromagnetic Plates, IEEE Transactions on Magnetics, Jul. 1979, 15(4):1174-1181, IEEE.
Hochmair, Erwin S., System Optimization for Improved Accuracy in Transcutaneous Signal and Power Transmission, IEEE Transactions on Biomedical Engineering, Feb. 1984,BME-31(2):177-186, IEEE.
Green, A. W. et at., 10kHz Inductively coupled power transfer—concept and control, Power Electronics and Variable-Speed Drives, Oct. 26-28, 1994, 399:694-699, IET.
Boys, J.T. et al., Stability and control of inductively coupled power transfer systems, IEE Proceedings—Electric Power Applications, Jan. 2000, 147(1):37-43, IET.
Boys, J.T. et al., Critical Q analysis of a current-fed resonant converter for ICPT applications, Electronics Letters, Aug. 17, 2000, 36(17):1440-1442, IEE.
Kim, Chang-Gyun et al., Design of a Contactless Battery Charger for Cellular Phone, IEEE Transactions on Industrial Electronics, Dec. 2001, 48(6):1238-1247, IEEE.
Jang, Yungtaek et al., A Contactless Electrical Energy Transmission System for Portable-Telephone Battery Chargers, IEEE Transactions on Industrial Electronics, Jun. 2003, 50(3):520-527, IEEE.
Choi, Byungcho et al., Design and Implementation of Low-Profile Contactless Battery Charger Using Planar Printed Circuit Board Windings as Energy Transfer Device, IEEE Transactions on Industrial Electronics, Feb. 2004, 51(1):140-147, IEEE.
Hui, S.Y,R. et al., A New Generation of Universal Contactless Battery Charging Platform for Portable Consumer Electronic Equipment, IEEE Transactions on Power Electronics, May 2005, 20(3):620-627, IEEE.
Elliott, Grant A.J. et al., A New Concept: Asymmetrical Pick-Ups for Inductively Coupled Power Transfer Monorail Systems, IEEE Transactions on Magnetics, Oct. 2006, 42(10):3389-3391, IEEE.
Liu, Xun et al., Simulation Study and Experimental Verification of a Universal Contactless Battery Charging Platform With Localized Charging Features, IEEE Transactions on Power Electronics, Nov. 2007, 22(6):2202-2210, IEEE.
Kissin, Michael L. G. et al., Interphase Mutual Inductance in Polyphase Inductive Power Transfer Systems, IEEE Transactions on Industrial Electronics, Jul. 2009, 56(7):2393-2400, IEEE.
Kim, N. Y. et al., Adaptive frequency with power-level tracking system for efficient magnetic resonance wireless power transfer, Electronic Letters, Apr. 12, 2012, 48(8):452-454, IET.
Hui, S.Y.R. et al., A Critical Review of Recent Progress in Mid-Range Wireless Power Transfer, IEEE Transactions on Power Electronics, Sep. 2014, 29(9):4500-4511, IEEE.
Sample, A.P. et al., "Enabling Seamless Wireless Power Delivery in Dynamic Environments", Proceedings of the IEEE, Jun. 2013, 101(6):1343-1358, IEEE.
Zhong, W. et al., "General Analysis on the Use of Tesla's Resonators in Domino Forms for Wireless Power Transfer", IEEE Transactions on Industrial Electronics, Jan. 2013, 60(1):261-270, 2011 IEEE.

* cited by examiner

METHODS FOR PARAMETER IDENTIFICATION, LOAD MONITORING AND OUTPUT POWER CONTROL IN WIRELESS POWER TRANSFER SYSTEMS

CROSS-REFERENCE TO RELATED APPLICATIONS

This application is the U.S. national stage application of International Patent Application No. PCT/CN2014/083775, filed Aug. 6, 2014, which claims priority to U.S. Provisional Patent Application No. 61/862,627, filed Aug. 6, 2013, the disclosures of each of which are incorporated herein by reference in their entirety.

BACKGROUND OF THE INVENTION

Technical Field

The present disclosure relates to the control of the output power for wireless power transfer systems.

Description of Related Art

Wireless power transfer based on the magnetic resonance and near-field coupling of two loop resonators was reported by Nicola Tesla a century ago. N. Tesla, "Apparatus for transmitting electrical energy," U.S. Pat. No. 1,119,732, (Dec. 1, 1914). As pioneered by Tesla, wireless power transfer can be radiative or non-radiative depending on the energy transfer mechanisms. Radiative power can be emitted from an antenna and propagates through a medium (such as vacuum or air) over long distance (i.e. many times larger than the dimension of the antenna) in the form of electromagnetic waves. However, due to the omni-directional nature of the radiative power emission, the energy efficiency of power transmission is very low. Non-radiative wireless power transfer relies on the near-field magnetic coupling of conductive loops and can be classified as short-range and mid-range applications. Herein the term mid-range applications refer to the situation where the transmission distance between the power source and the load is larger than the dimension of the coil-resonators.

It should be noted that wireless power transfer has been applied extensively in ac machines, which were also pioneered by Tesla. See, Robert Lomas, "The man who invented the twentieth century—Nikola Tesla—Forgotten Genius of Electricity," Headline (1999), ISBN 0 7472 6265 9, p. 146. Using a cage induction machine as an example, energy is transferred from the excited stator windings across the air gap to the rotor cage. Energy transfer via coupled windings is the basic principle used in electric machines. Therefore, wireless power systems can be mathematically described by electric circuit theory for magnetically coupled circuits.

Wireless power transfer has been an active research topic for transcutaneous energy systems for medical implants since the 1960's. See, J. C. Schuder, H. E. Stephenson, and J. F. Townsend, "High level electromagnetic energy transfer through a closed chestwall," *IRE Int. Conv. Rec.*, pt. 9, vol. 9, pp. 119-126, (1961); W. H. Ko, S. P. Liang, and C. D. F. Fung, "Design of rf-powered coils for implant instruments," *Med. Biol. Eng. Comput.*, vol. 15, pp. 634-640, (1977); E. Hochmair, "System optimization for improved acuracy in transcutaneous signal and power transmission", *IEEE Trans. Biomedical Engineering*, vol. BME-31, no. 2, pp. 177-186, (February 1984); B. Choi, J. Nho, H. Cha, T. Ahn and S. Choi, "Design and implementation of low-profile contactless battery charger using planar printed circuit board windings as energy transfer device," *IEEE Trans. Industrial Electronics*, vol. 51, no. 1, pp. 140-147, (February 2004); and Y. Jang and M. M. Jovanovic, "A contactless electrical energy transmission system for portable-telephone battery chargers", *IEEE Trans. Industrial Electronics*, vol. 50, no. 3, pp. 520-527, (June 2003).

This research has also involved induction heaters since the 1970's. See, W. G. Hurley and J. Kassakian, "Induction heating of circular ferromagnetic plates", *IEEE Trans. Magnetics*, vol. 15, no. 4, pp. 1174-1181, (July 1979). For modern short-range applications, the inductive power transfer (IPT) systems have attracted much attention since the 1990's. A. W. Green and J. T. Boys, "10 kHz inductively coupled power transfer-concept and control," *Proc. ICPE-VSD*, (1994), pp. 694-699; J. T. Boys, G. A. Covic and A. W. Green, "Stability and control of inductively coupled power transfer systems", *Proc. Electric Power Applications*, (2000), vol. 147, no. 1, pp. 37-43; J. T. Boys, A. P. Hu and G. A. Covic, "Critical Q analysis of a current-fed resonant converter for ICPT applications," *Electronics Letters*, vol. 36, no. 17, pp. 1440-1442, (2000); G. A. J. Elliott, G. A. Covic, D. Kacprzak and J. T. Boys, "A New Concept: Asymmetrical Pick-Ups for Inductively Coupled Power Transfer Monorail Systems," *IEEE Trans. Magnetics*, vol. 42, no. 10, pp. 3389-3391, (2006); and M. L. G. Kissin, J. T. Boys and G. A. Covic, "Interphase Mutual Inductance in Polyphase Inductive Power Transfer Systems," *IEEE Trans. Industrial Electronics*, vol. 56, no. 7, pp. 2393-2400, (2009). The wireless charging systems for portable equipment, such as mobile phones have attracted much attention since the 2000's. B. Choi, J. Nho, H. Cha, T. Ahn and S. Choi, "Design and implementation of low-profile contactless battery charger using planar printed circuit board windings as energy transfer device," *IEEE Trans. Industrial Electronics*, vol. 51, no. 1, pp. 140-147, (February 2004); Y. Jang and M. M. Jovanovic, "A contactless electrical energy transmission system for portable-telephone battery chargers," *IEEE Trans. Industrial Electronics*, vol. 50, no. 3, pp. 520-527, (June 2003); C.-G. Kim, D. H. Seo, J. S. You, J. H. Park and B. H. Cho, "Design of a contactless battery charger for cellular phone," *IEEE Trans. Industrial Electronics*, vol. 48, no. 6, pp. 1238-1247, (December 2001); S. Y. R. Hui and W. C. Ho, "A new generation of universal contactless battery charging platform for portable Consumer Electronic equipment," *IEEE Trans. Power Electronics*, vol. 20, no. 3, pp. 620-627, (May 2005); X. Liu and S. Y. R. Hui, "Simulation Study and Experimental Verification of a Contactless Battery Charging Platform with Localized Charging Features," *IEEE Trans. Power Electronics*, vol. 22, no. 6, pp. 2202-2210, (November 2007); and S. Y. R. Hui, "Planar Inductive Battery Charging System", U.S. Pat. No. 7,576,514, 2009. Wireless charging technology for portable electronic devices has reached the commercialization stage through the launch of the "Qi" Standard by the Wireless Power Consortium, now comprising over 135 companies worldwide. See the Wireless Power Consortium Website, available at: http://www.wirelesspowerconsortium.com.

The launch of the world first wireless power standard Qi by the Wireless Power Consortium for portable electronics products has sped up research and development activities in wireless power transfer. Recent wireless power research activities focus on both short-range applications and mid-range applications. In general, wireless power transfer systems (WPTS) can be classified as 2-coil systems, 4-coil systems, systems with relay resonators and wireless power domino-resonator systems. S. Y. R. Hui, W. X. Zhong and C.

K. Lee, "A critical review on recent progress of mid-range wireless power transfer," *IEEE Transactions on Power Electronics* (in press)

At present, a great deal of research is focused on improving the performance of wireless power transfer systems in order to increase the transfer distance, improve the efficiency and widen the operating frequency. All of these purposes are based on one thing, a well-known wireless power transfer system in which we know the topology of the system, all of the parameters of the components, the characteristics of the load, and the positions and directions of each coil. If so, it is easy to find the maximum efficiency operating point or maximum power transfer point, or the optimal operating point for other purposes. The biggest difficulty is how to find out the exact value of all the parameters of a given system, since as an extremely high order system, the slight difference between the predicted value and the real value of the parameters may lead to totally different performance at a given operating point, and some of these parameters cannot be measured precisely in an easy way.

On the other hand, even if we know all the parameters of the WPT system, the load may be dynamic and will change at any time. In order to operate the system always at the optimal point, monitoring of the impedance of the load at real time is required. Previously, a research team reported the use of a wireless communication method to transmit the load conditions as feedback information to the input power controller. N. Y. Kim, K. Y. Kim, J. Choi and C. W. Kim, "Adaptive frequency with power-level tracking system for efficient magnetic resonance wireless power transfer," *Electronics Letters*, Vol. 48, No. 8, (April 2012), page(s): 452-454. This is a traditional approach that needs a wireless communication system, which may increase the cost of such overall system. In addition, the reported method does not involve any system parameter identification.

SUMMARY OF THE INVENTION

The present disclosure is directed methods for identifying the system parameters and monitoring (including controlling the power of) the load of a wireless power transfer system without using any wired or wireless communication system from the load side for feedback control.

According to the first aspect of the present disclosure, it provides a method for identifying impedance related parameters in a wireless power transfer (WPT) system including n coils, including: determining optimum values of the impedance related parameters based on a set of measured input impedance by applying an evolutionary algorithm to solve optimum solutions. Wherein the set of measured input impedance includes an input impedance vector $\vec{Z}=(Z_1, Z_2, \ldots, Z_{m-1}, Z_m)$, each input impedance in the vector ($Z_k$) measured at different frequencies $f_k$, (k=1, 2, m); and the impedance related parameters includes $d_{l,l+1}$ representing a distance between the l-th coil and the l+1 coil (l=1, 2, n−1) and $C_i$ representing a capacitance of the capacitor connected to the i-th coil (i=1, 2, . . . n).

According to the second aspect of the present disclosure, it provides a method for monitoring a load $Z_L$ in a wireless power transfer (WPT) system including n coils, comprises: sensing an input voltage $U_1$ and an input current $I_1$ of a transmitter coil of the n coils; determining a set of measured input impedance based on the sensed input voltage $U_1$ and the sensed input current $I_1$; identifying impedance related parameters according to the method of the first aspect of the present disclosure; and determining the load only based on the sensed input voltage $U_1$, the sensed input current $I_1$, and the identified impedance related parameters.

According to the third aspect of the present disclosure, it provides a method for controlling output power in a wireless power transfer (WPT) system including n coils, comprises: (a) sensing an input voltage $U_1$ and an input current $I_1$ of a transmitter coil of the n coils; (b) determining whether impedance related parameters in the WPT system are known, wherein the impedance related parameters includes $d_{l,l+1}$ representing the distance between the l-th coil and the l+1 coil (l=1, 2, . . . , n−1) and $C_i$ representing the capacitance of the capacitor connected to the i-th coil (i=1, 2, . . . n): (b.1) if the result of the step of determining is yes, the method further comprises: based on the sensed input voltage $U_1$, the sensed input current $I_1$, and the known impedance related parameters, estimating load $Z_L$ of the WPT system, output current of the WPT system $I_n$, power $P_{out}$ of the load $Z_L$, output voltage $U_o$ of the WPT system, and efficiency η of the WPT system according to the method of the second aspect of the present disclosure; (b.2) if the result of the step of determining is no, the method further comprises: determining a set of measured input impedance based on the sensed input voltage $U_1$ and the sensed input current $I_1$, identifying impedance related parameters in the WPT system according to one of the method of the first aspect of the present disclosure, based on the sensed input voltage $U_1$, the sensed input current $I_1$, and the identified impedance related parameters, estimating load $Z_L$ of the WPT system, output current of the WPT system $I_n$, power $P_{out}$ of the load $Z_L$, output voltage $U_o$ of the WPT system, and efficiency η of the WPT system according to the method of the second aspect of the present disclosure; (c) generating feedback information based on the estimated parameters in step (b.1) or (b.2); and (d) controlling the operations of the transmitter coil based on the generated feedback information.

BRIEF DESCRIPTION OF THE DRAWINGS

The foregoing and other features of the present disclosure will be more readily apparent from the following detailed description and drawings of illustrative embodiments of the disclosure wherein like reference numerals refer to like parts throughout the various figures unless otherwise specified and in which.

DETAILED DESCRIPTION

One aspect of this disclosure focuses on parameter identification for a wireless power transfer system.

Figure 1:
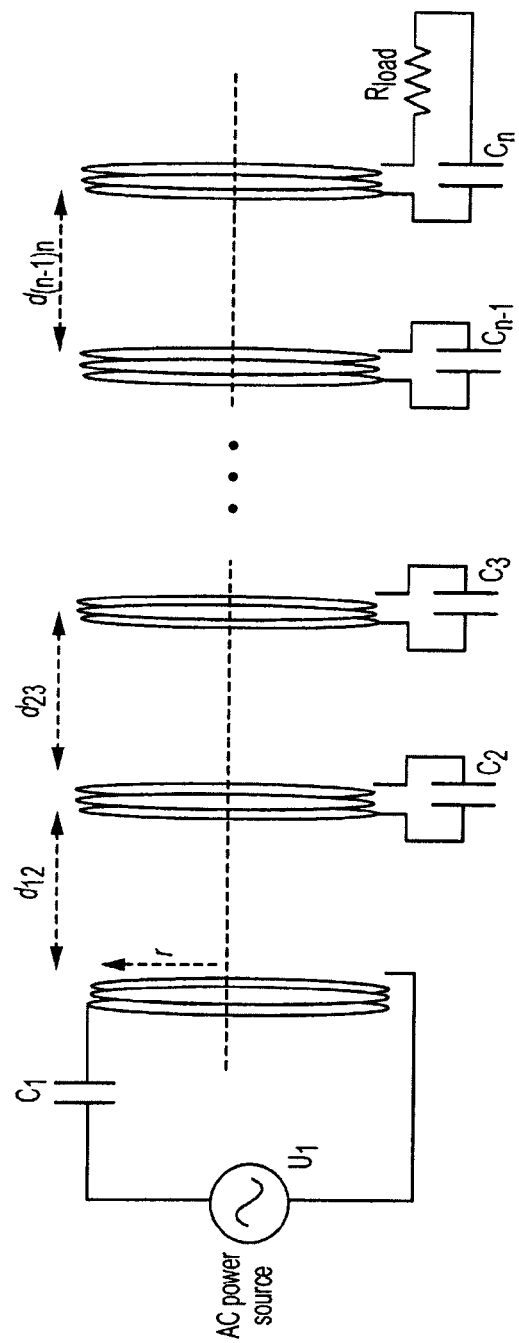
FIG. 1 is a schematic of an n-Ring system for wireless power transfer.

For a domino wireless power transfer system with n-coils as shown in FIG. 1, if we assume $L_i$ is the self-inductance of the $i^{th}$ coil, and $M_{ij}$ is mutual-inductance between the $i^{th}$ coil and the $j^{th}$ coil, then the system could be described using equation (1). Note in FIG. 1 that the load resistor is connected in series with the last coil-resonator in the following formulation. But the principle of this disclosure can also apply to the case where the load is connected across the capacitor of the last LC resonator.

$$\begin{bmatrix} U_1 \\ 0 \\ \vdots \\ 0 \\ 0 \end{bmatrix} = \begin{bmatrix} R_1 + j\left(\omega L_1 - \frac{1}{\omega C_1}\right) & j\omega M_{12} & \cdots & j\omega M_{1(n-1)} & j\omega M_{1n} \\ j\omega M_{21} & R_2 + j\left(\omega L_2 - \frac{1}{\omega C_2}\right) & \cdots & j\omega M_{2(n-1)} & j\omega M_{2n} \\ \vdots & \vdots & \ddots & \vdots & \vdots \\ j\omega M_{(n-1)1} & j\omega M_{(n-1)2} & \cdots & R_{n-1} + j\left(\omega L_{n-1} - \frac{1}{\omega C_{n-1}}\right) & j\omega M_{12} \\ j\omega M_{n1} & j\omega M_{(n-1)2} & \cdots & j\omega M_{(n-1)(n-1)} & R_n + R_l + j\left(\omega L_n - \frac{1}{\omega C_n}\right) \end{bmatrix} \begin{bmatrix} I_1 \\ I_2 \\ \vdots \\ I_{n-1} \\ I_n \end{bmatrix} \quad (1)$$

A. Parameter Identification

If we know all the parameters in the matrix in equation (1), then we can calculate the input impedance of the system for each frequency along the frequency axis, i.e., we can get a set of impedance values at different frequencies: $Z_{f1}$, $Z_{f2}$, ... $Z_{fm}$, where $f_i$ is one of the different frequencies, and $Z_{fi}$ is the input impedance at $f_i$. Then we have equation (2):

$$(Z_1, Z_2, \ldots, Z_{m-1}, Z_m) = f\begin{pmatrix} L_1, L_2, \ldots, L_{n-1}, L_n, \\ M_{12}, M_{23}, \ldots, M_{(n-2)(n-1)}, M_{(n-1)n}, \\ C_1, C_2, \ldots, C_{n-1}, C_n, \\ R_1, R_2, \ldots, R_{n-1}, R_n, \\ R_{load} \end{pmatrix} \quad (2)$$

Since the coils in our domino system are identical to each other and the self-inductance could be accurately calculated, we can treat $L_1$ through $L_n$, and the coil resistance, $R_1$ through $R_n$ as constant values. Meanwhile, we can treat the mutual inductances $M_{12}$, $M_{23}$, $M_{(n-1)n}$ as functions of the distances between each coil pair, $d_{12}$, $d_{23}$, ..., $d_{(n-1)n}$). Then equation (2) may be replaced by equation (3) as follows:

$$(Z_1, Z_2, \ldots, Z_{m-1}, Z_m) = f\begin{pmatrix} f_{12}, d_{23}, \ldots, d_{(n-2)(n-1)}, d_{(n-1)n}, \\ C_1, C_2, \ldots, C_{n-1}, C_n, \\ R_{load} \end{pmatrix} \quad (3)$$

For a given system, the input impedance set $(Z_1, Z_2, \ldots, Z_{m-1}, Z_m)$ could easily be measured experimentally.

Genetic Algorithm (GA) approach is used to search for the optimal values of $d_{12}$, $d_{23}$, ..., $d_{(n-1)n}$, $C_1$, $C_2$, ..., $C_{(n-1)}$, $C_n$ and $R_{load}$. With the help of a set of measured input impedance $(Z_1, Z_2, \ldots, Z_{m-1}, Z_m)$ at different frequencies, the GA can be used to obtain the optimum solutions for the following optimum problem:

$$J\begin{pmatrix} d_{12}, d_{23}, \ldots, d_{(n-2)(n-1)}, d_{(n-1)n}, \\ C_1, C_2, \ldots, C_{n-1}, C_n, \\ R_{load} \end{pmatrix} = \quad (4)$$

-continued $$\min\left[\sum_{1}^{m}((|Z_i| - |Z_i^*|)^2 + (\theta_i - \theta_i^*)^2)\right]$$

Where $|Z_i|$ and $\theta_i$ are magnitude and angular value of the measured input impedance, while $|Z_i^*|$ and $\theta_i^*$ are the simulated magnitude and angular value of the input impedance.

In a representative example of the present disclosure for identifying the parameters for wireless power transfer system by using evolutionary algorithm, a 3-coil-domino system and an 8-coil-domido system were used. For each domino system, different coil distance and different load resistances were used to check whether this method could be used at different conditions. The different experimental conditions are listed in Table 1 and Table 2. The simulation results are listed in Table 3 and Table 4.

TABLE 1

| experiments for 3-coil-domino system | | | | | | |
|---|---|---|---|---|---|---|
| No. | c1 | c2 | c3 | d12 | d23 | Rload |
| 1 | #1 | #2 | #3 | 0.20 m | 0.20 m | 11.8 Ohm |
| 2 | #1 | #2 | #3 | 0.20 m | 0.25 m | 11.8 Ohm |
| 3 | #1 | #2 | #3 | 0.20 m | 0.20 m | 49.9 Ohm |
| 4 | #1 | #2 | #3 | 0.20 m | 0.25 m | 49.9 Ohm |

TABLE 2

| experiments for 8-coil-domino system | | | | | | | | |
|---|---|---|---|---|---|---|---|---|
| | c1 | c2 | c3 | c4 | c5 | c6 | c7 | c8 |
| No. 1 | #4 | #5 | #6 | #7 | #8 | #9 | #10 | #11 |
| | d12 | d23 | d34 | d45 | d56 | d67 | d78 | Rload |
| | 0.15 m | 0.15 m | 0.15 m | 0.15 m | 0.15 m | 0.15 m | 0.15 m | 11.8 Ohm |

TABLE 2-continued experiments for 8-coil-domino system

| | c1 | c2 | c3 | c4 | c5 | c6 | c7 | c8 |
|---|---|---|---|---|---|---|---|---|
| No. 2 | #4 | #5 | #6 | #7 | #8 | #9 | #10 | #11 |
| | d12 | d23 | d34 | d45 | d56 | d67 | d78 | Rload |
| | 0.15 m | 0.15 m | 0.15 m | 0.15 m | 0.15 m | 0.15 m | 0.25 m | 11.8 Ohm |
| No. 3 | #4 | #5 | #6 | #7 | #8 | #9 | #10 | #11 |
| | d12 | d23 | d34 | d45 | d56 | d67 | d78 | Rload |
| | 0.15 m | 0.15 m | 0.15 m | 0.15 m | 0.15 m | 0.15 m | 0.15 m | 49.9 Ohm |
| No. 4 | #4 | #5 | #6 | #7 | #8 | #9 | #10 | #11 |
| | d12 | d23 | d34 | d45 | d56 | d67 | d78 | Rload |
| | 0.15 m | 0.15 m | 0.15 m | 0.15 m | 0.15 m | 0.15 m | 0.25 m | 49.9 Ohm |

TABLE 3 simulation results for 3-coil-domino system

| No. | c1 | c2 | c3 | d12 | d23 |
|---|---|---|---|---|---|
| 1 | 1.0191 | 1.0040 | 1.0197 | 0.2021 | 0.1984 |
| 2 | 1.0180 | 1.0040 | 1.0195 | 0.2016 | 0.2494 |
| 3 | 1.0192 | 1.0031 | 1.0215 | 0.1890 | 0.2167 |
| 4 | 1.0192 | 1.0036 | 1.0211 | 0.2042 | 0.2531 |

TABLE 4 simulation results for 8-coil-domino system

| | c1 | c2 | c3 | c4 | c5 | c6 | c7 | c8 |
|---|---|---|---|---|---|---|---|---|
| No. 1 | 1.0166 | 1.0187 | 1.0187 | 1.0174 | 0.9695 | 1.0080 | 1.0026 | 1.0233 |
| | d12 | d23 | d34 | d45 | d56 | d67 | d78 | |
| | 0.1523 | 0.1480 | 0.1413 | 0.1571 | 0.1504 | 0.1477 | 0.1520 | |
| No. 2 | 1.0116 | 1.0170 | 1.0202 | 1.0203 | 0.9700 | 1.0081 | 1.0062 | 1.0177 |
| | d12 | d23 | d34 | d45 | d56 | d67 | d78 | |
| | 0.1529 | 0.1493 | 0.1414 | 0.1586 | 0.1494 | 0.1460 | 0.2493 | |
| No. 3 | 1.0183 | 1.0184 | 1.0160 | 1.0190 | 0.9670 | 1.0092 | 1.0044 | 1.0124 |
| | d12 | d23 | d34 | d45 | d56 | d67 | d78 | |
| | 0.1464 | 0.1516 | 0.1530 | 0.1488 | 0.1442 | 0.1487 | 0.1468 | |
| No. 4 | 1.0165 | 1.0160 | 1.0143 | 1.0121 | 0.9701 | 1.0191 | 1.0099 | 1.0024 |
| | d12 | d23 | d34 | d45 | d56 | d67 | d78 | |
| | 0.1471 | 0.1513 | 0.1519 | 0.1465 | 0.1482 | 0.1495 | 0.2506 | |

Figure 2A:
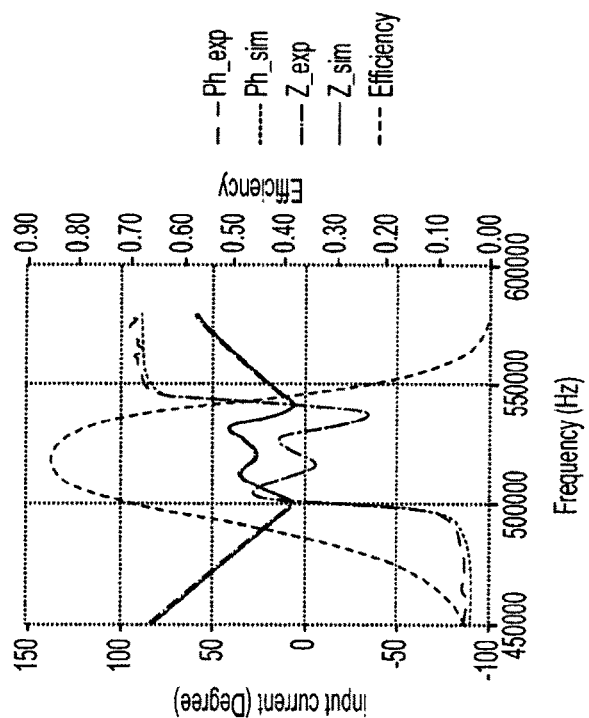
FIGS. 2(*a*) and 2(*b*) are graphs of experimental and simulation results for the input impedance of coil arrangements No. 1 and No. 2, respectively, in Table 1 for 3-coil domino systems.
Figure 2B:
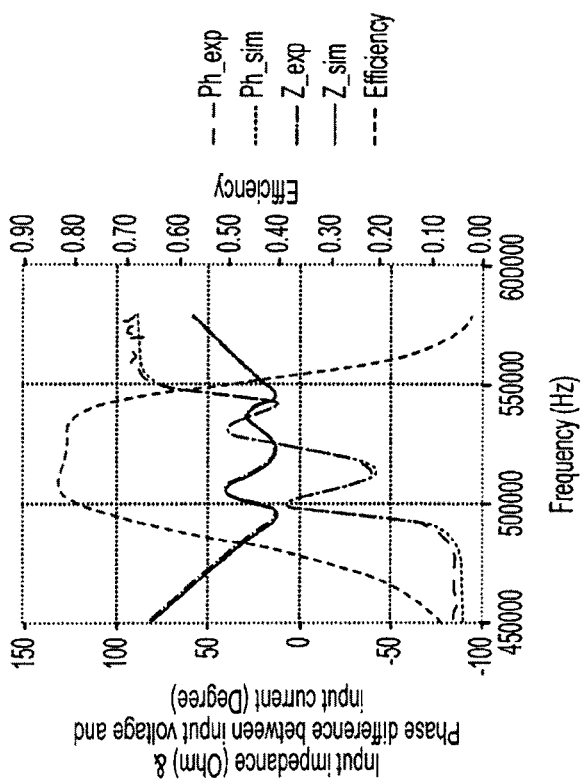
Figure 3A:
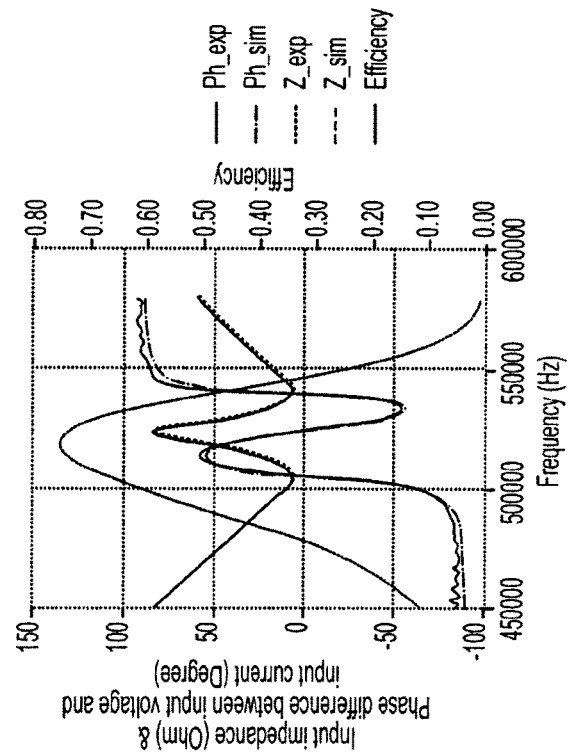
FIGS. 3(*a*) and 3(*b*) are graphs of experimental and simulation results for the input impedance of coil arrangements No. 3 and No. 4, respectively, in Table 1 for 3-coil domino systems.
Figure 3B:
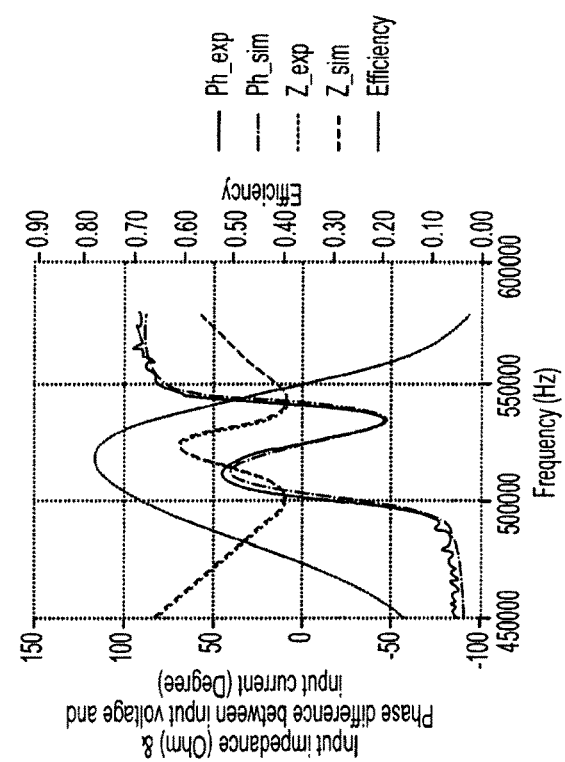
Figure 4A:
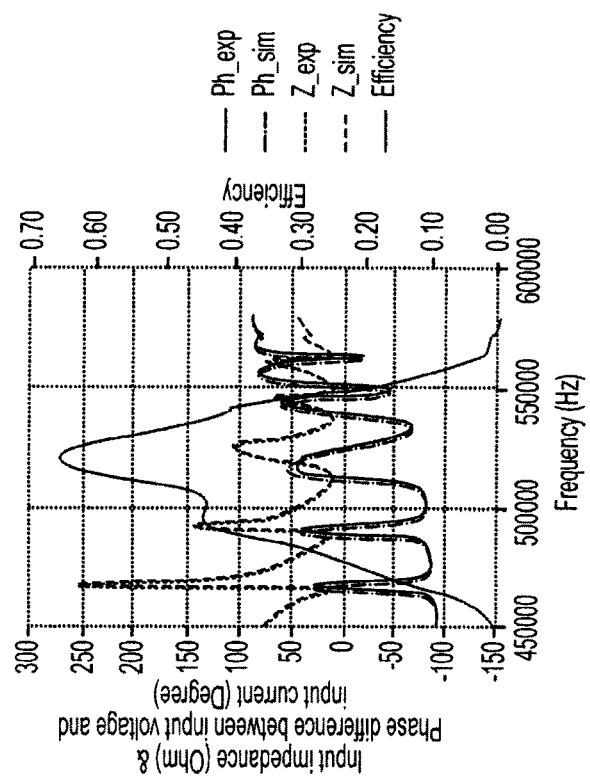
FIGS. 4(*a*) and 4(*b*) are graphs of experimental and simulation results for the input impedance of coil arrangements No. 1 and No. 2, respectively, in Table 2 for 8-coil domino systems.
Figure 4B:
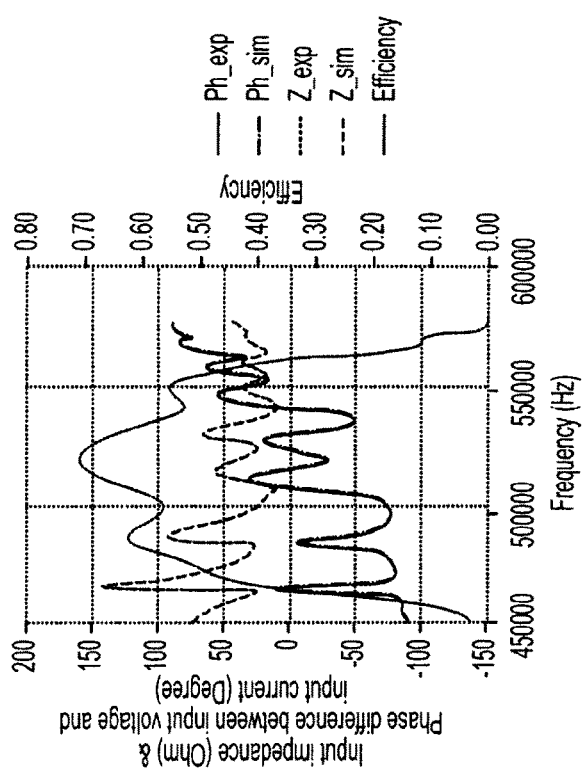
Figures 5A, 5B:
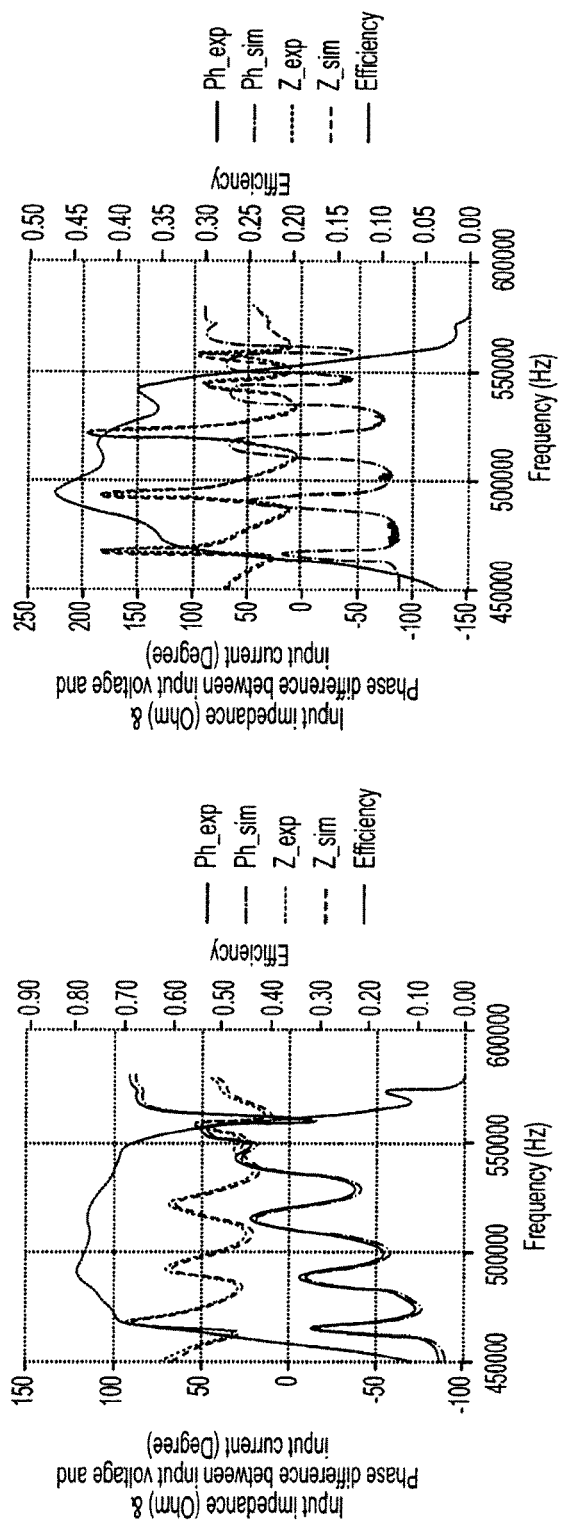
FIGS. 5(*a*) and 5(*b*) are graphs of experimental and simulation results for the input impedance of coil arrangements No. 3 and No. 4, respectively, in Table 2 for 8-coil domino systems.

FIG. 2 and FIG. 3 are the experimental and simulation input impedance comparison for a 3-coil-domino system. FIG. 4 and FIG. 5 are the experimental and simulated input impedance comparison for 8-coil-domino system. Also the simulated efficiencies are plotted in these figures. In particular, FIGS. 2(a) and 2(b) show the experimental and simulation input impedance comparison of coil parameters No. 1 and No. 2, respectively, from the experiment in Table 1 for the 3-coil-domino systems. FIGS. 3(a) and 3(b) show the experimental and simulation input impedance comparison of coil parameters No. 3 and No. 4, respectively, from the experiment in Table 1 for the 3-coil-domino systems. FIGS. 4(a) and 4(b) show the experimental and simulation input impedance comparison of coil parameters No. 1 and No. 2, respectively, from the experiment in Table 2 for the 8-coil-domino systems. Finally, FIGS. 5(a) and 5(b) show the experimental and simulation input impedance comparison of coil parameters No. 3 and No. 4, respectively, from the experiment in Table 2 for the 8-coil-domino systems.

B. Load Monitoring without Direct Output Information Feedback

Another aspect of the present disclosure focuses on load monitoring for wireless power transfer system.

In equation (1), since all the parameters, $L_1$ through $L_n$, $R_1$ through $R_n$, $M_{12}, M_{23}, \ldots M_{(n-1)n}$ and $C_1, C_2, \ldots, C_n$ are identified in the first aspect, the load impedance $R_l$ is the only obstacle which prevents simulation of the system and finding the optimal operating point, such as maximum power transfer or maximum efficiency of the system for a given load. It is not possible to assume the load always has the same impedance. Thus, the load must be continually sensed and the load impedance value renewed for calculating a new operating frequency in order to ensure the system always operates at the optimal point.

An easy way to solve this problem involves rewriting equation (1) as equation (5) and equation set (6), and then equation set (7), where $Z_{ij}$ is the function of $R_l$ through $R_n$, $M_{12}, M_{23}, \ldots, M_{(n-1)n}$, and $C_1, C_2, \ldots, C_n$, $Z_L$ is the impedance of the load at a given frequency.

$$\begin{bmatrix} U_1 \\ 0 \\ \vdots \\ 0 \\ 0 \end{bmatrix} = \begin{bmatrix} Z_{11} & Z_{12} & \ldots & Z_{1(n-1)} & Z_{1n} \\ Z_{21} & Z_{22} & \ldots & Z_{2(n-1)} & Z_{2n} \\ \vdots & \vdots & \ddots & \vdots & \vdots \\ Z_{(n-1)1} & Z_{(n-1)2} & \ldots & Z_{(n-1)(n-1)} & Z_{(n-1)n} \\ Z_{n1} & Z_{n2} & \ldots & Z_{n(n-1)} & Z_{nn} + Z_L \end{bmatrix} \begin{bmatrix} I_1 \\ I_2 \\ \vdots \\ I_{n-1} \\ I_n \end{bmatrix} \quad (5)$$

$$U_1 = Z_{11}I_1 + Z_{12}I_2 + \ldots + Z_{1(n-1)}I_{(n-1)} + Z_{1n}I_n \quad (6)$$
$$0 = Z_{21}I_1 + Z_{22}I_2 + \ldots + Z_{2(n-1)}I_{(n-1)} + Z_{2n}I_n$$
$$\vdots$$
$$0 = Z_{(n-1)1}I_1 + Z_{(n-1)2}I_2 + \ldots + Z_{(n-1)(n-1)}I_{(n-1)} + Z_{(n-1)n}I_n$$
$$0 = Z_{n1}I_1 + Z_{n2}I_2 + \ldots + Z_{n(n-1)}I_{(n-1)} + Z_{nn}I_n + Z_LI_n$$

-continued $$U_1 - Z_{11}I_1 = Z_{12}I_2 + \ldots + Z_{1(n-1)}I_{(n-1)} + Z_{1n}I_n \quad (7)$$
$$-Z_{21}I_1 = Z_{22}I_2 + \ldots + Z_{2(n-1)}I_{(n-1)} + Z_{2n}I_n$$
$$\vdots$$
$$-Z_{(n-1)1}I_1 = Z_{(n-1)2}I_2 + \ldots + Z_{(n-1)(n-1)}I_{(n-1)} + Z_{(n-1)n}I_n$$
$$-Z_{n1}I_1 = Z_{n2}I_2 + \ldots + Z_{n(n-1)}I_{(n-1)} + Z_{nn}I_n + Z_LI_n$$

Equation set (7) could be rewritten in matrix form as equation (8), $$\begin{bmatrix} U_1 - Z_{11}I_1 \\ -Z_{21}I_1 \\ \vdots \\ -Z_{(n-1)1}I_1 \\ -Z_{n1}I_1 \end{bmatrix} = \begin{bmatrix} Z_{12} & \ldots & Z_{1(n-1)} & Z_{1n} & 0 \\ Z_{22} & \ldots & Z_{2(n-1)} & Z_{2n} & 0 \\ \vdots & \vdots & \ddots & \vdots & \vdots \\ Z_{(n-1)2} & \ldots & Z_{(n-1)(n-1)} & Z_{(n-1)n} & 0 \\ Z_{n2} & \ldots & Z_{n(n-1)} & Z_{nn} & 1 \end{bmatrix} \begin{bmatrix} I_2 \\ I_3 \\ \vdots \\ I_n \\ Z_LI_n \end{bmatrix} \quad (8)$$

In equation (8), $Z_{11}$, $Z_{12}$, ... $Z_{nn}$ are a function of frequency and known parameters, $U_1$ and $I_1$ are the input voltage and input current vector to the transmitter and could be measured easily, only $I_2$, $I_3$, ... $I_n$, $Z_LI_n$ are unknowns. Then we get the solution of the matrix as equation (9).

$$\begin{bmatrix} I_2 \\ I_3 \\ \vdots \\ I_n \\ Z_LI_n \end{bmatrix} = \begin{bmatrix} Z_{12} & \ldots & Z_{1(n-1)} & Z_{1n} & 0 \\ Z_{22} & \ldots & Z_{2(n-1)} & Z_{2n} & 0 \\ \vdots & \vdots & \ddots & \vdots & \vdots \\ Z_{(n-1)2} & \ldots & Z_{(n-1)(n-1)} & Z_{(n-1)n} & 0 \\ Z_{n2} & \ldots & Z_{n(n-1)} & Z_{nn} & 1 \end{bmatrix}^{-1} \begin{bmatrix} U_1 - Z_{11}I_1 \\ -Z_{12}I_1 \\ \vdots \\ -Z_{1(n-1)}I_1 \\ -Z_{1n}I_1 \end{bmatrix} \quad (9)$$

It should be noted that the inverse matrix in (9) has the unique form:

$$\begin{bmatrix} Z_{12} & \ldots & Z_{1n} & 0 \\ Z_{22} & \ldots & Z_{2n} & 0 \\ \vdots & \ddots & \ddots & \vdots \\ Z_{n2} & \ldots & Z_{nn} & 1 \end{bmatrix}$$

where the last column has zero elements except for the last element.

Normally, the ac power source comes from the output of a power inverter (which is a dc-ac power converter) fed by a dc voltage source ($U_{dc}$) with very low source resistance. The dc power delivered by this dc voltage source can be considered as the input power $P_{in}$. To solve (9), the power balance equation can be used, i.e., the scalar relationship of the input power can be used as follows:

$$P_{in}=U_{dc}I_{dc}=\eta_{inv}U_1I_1\cos(\phi) \quad (10)$$

where $\eta_{inv}$ is the energy efficiency of the power inverter, $I_{dc}$ is the output current of the dc voltage source and $\phi$ is the phase angle between $U_1$ and $I_1$. $U_1$ is the fundamental component of the ac driving voltage of the transmitter coil if such driving voltage is not sinusoidal.

The magnitude of $U_1$ and $I_1$ can be easily measured, e.g. with the use of peak detectors for their scale-down signals. Since the input information of $P_{in}$, $U_1$ and $I_1$ of equation (10) can be determined, $\cos(\phi)$ and $\phi$ can be determined.

$$\phi = \cos^{-1}\left(\frac{P_{in}}{\eta_{inv}U_1I_1}\right) \quad (11)$$

This angle can be leading or lagging, which can be determined by comparing the scaled-down waveforms of $U_1$ and $I_1$ with a zero voltage reference in comparators. The rising voltage edges of the comparators for $U_1$ and $I_1$ can be used to determine whether $I_1$ is leading or lagging $U_1$.

If $U_1$ is used as the reference vector in the rotating frame, $I_1$ can be represented in complex form with respect to $U_1$ in equation (9). This is a very important point because only the magnitude and phase relationships of $U_1$ and $I_1$ in equation (9) need to be known. Such a matrix equation can now be solved as a set of complex equations. It is not necessary to sample the instantaneous values of $U_1$ and $I_1$, and therefore fast sampling and fast computational requirements are totally eliminated in this disclosure. For example, for an operating frequency of 500 kHz, if the instantaneous values of $U_1$ and $I_1$ are used in (9), the sampling frequency for $U_1$ and $I_1$ must be much higher than 500 kHz. However, if only the magnitudes of $P_{in}$, $U_1$ and $I_1$ are needed (as in one preferred approach explained previously), the sampling rate can be very low (e.g. 1 kHz). Therefore this approach greatly reduces the sampling frequency and costs and complexity of the control electronics. Of course, if fast computational controllers become available and economical, the sampled values of $U_1$ and $I_1$ can be used for solving (9). In this case, there is no needed to measure $P_{in}$ and only measurements of $U_1$ and $I_1$ are necessary.

Finally, the solution of $Z_L$ is:

$$Z_L = \frac{Z_LI_n}{I_n} \quad (12)$$

Based on equations (9) and (10), the load power can then be determined from:

$$P_{out}=I_n^2Re(Z_L) \quad (13)$$

The output voltage is:

$$U_o=Z_LI_n \quad (14)$$

Assuming that the power inverter has negligible power loss, the system energy efficiency is:

$$\eta = \frac{P_{out}}{P_{out} + \sum_{x=1}^{n} I_x^2 R_x} \text{ or} \quad (15)$$

$$\eta = \frac{P_{out}}{U_{in}I_{in}\cos\varphi}$$

where $\phi$ is the angle between $U_{in}$ and $I_{in}$.

Figure 6:
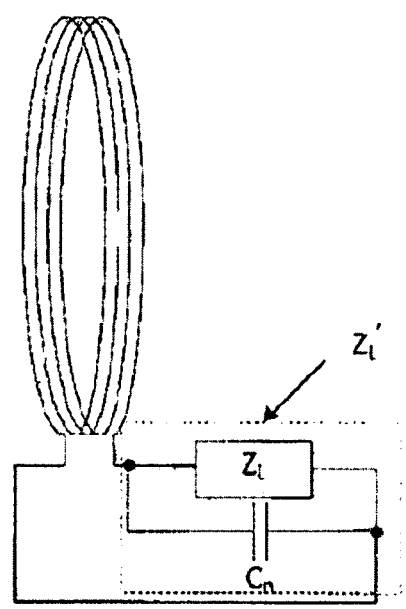
FIG. 6 is a schematic of a loaded resonator with the load connected in parallel with the resonant capacitor.

FIG. 6 is a schematic of the loaded resonator with the load connected in parallel with the resonant capacitor. If the loaded resonator has the load connected across the resonant capacitor as shown in FIG. 6, the load $Z_L$ and the paralleled capacitor $C_n$ are treated as a new load $Z_L'$, and all of the equations will be the same, except the $Z_{nn}$ and $Z_L$. Then equation (5) will be changed into equation (5a), equation (9) will be changed into equation (9a). Equation (12) will be changed into equation (12a), $$\begin{bmatrix} U_1 \\ 0 \\ \vdots \\ 0 \\ 0 \end{bmatrix} = \begin{bmatrix} Z_{11} & Z_{12} & \cdots & Z_{1(n-1)} & Z_{1n} \\ Z_{21} & Z_{22} & \cdots & Z_{2(n-1)} & Z_{2n} \\ \vdots & \vdots & \ddots & \vdots & \vdots \\ Z_{(n-1)1} & Z_{(n-1)2} & \cdots & Z_{(n-1)(n-1)} & Z_{(n-1)n} \\ Z_{n1} & Z_{n2} & \cdots & Z_{n(n-1)} & Z'_{nn} + Z'_L \end{bmatrix} \begin{bmatrix} I_1 \\ I_2 \\ \vdots \\ I_{n-1} \\ I_n \end{bmatrix} \quad (5a)$$

$$\begin{bmatrix} I_2 \\ I_3 \\ \vdots \\ I_n \\ Z'_L I_n \end{bmatrix} = \begin{bmatrix} Z_{12} & \cdots & Z_{1(n-1)} & Z_{1n} & 0 \\ Z_{22} & \cdots & Z_{2(n-1)} & Z_{2n} & 0 \\ \vdots & \ddots & \vdots & \vdots & \vdots \\ Z_{(n-1)2} & \cdots & Z_{(n-1)(n-1)} & Z_{(n-1)n} & 0 \\ Z_{n2} & \cdots & Z_{n(n-1)} & Z'_{nn} & 1 \end{bmatrix}^{-1} \begin{bmatrix} U_1 - Z_{11}I_1 \\ -Z_{12}I_1 \\ \vdots \\ -Z_{1(n-1)}I_1 \\ -Z_{1n}I_1 \end{bmatrix} \quad (9a)$$

$$Z'_L = \frac{Z'_L I_n}{I_n}$$

Since it is known that $Z'_L$ is the parallel impedance of $Z_L$ and $C_n$, the solution of $Z_L$ is:

$$Z_L = \frac{1}{\dfrac{1}{Z'_L} - j\omega c_n} \quad (12a)$$

To summarize the novel procedure for load monitoring without using direct feedback information, that is, based on the information of the input voltage ($U_{in}=U_1$) and input current ($I_{in}=I_1$) only, the following is the procedure:

1. Use the standard coupled circuit matrix equation (5) to mathematically describe the wireless power transfer system.
2. Note that only $U_1$ and $I_1$ are known, rearrange the matrix equation (5) to the form of equation (8) in which the column vector on the right-hand-side of the equation (8) consists of $I_2$ to $I_n$ and $Z_L I_n$, where $I_2$ is the current in the second coil, $I_n$ is the current in the receiver coil and $Z_L$ is the load impedance.
3. Then create the inverse matrix of equation (8) and obtain the matrix equation in the form of equation (9), which is the column vector mentioned in the previous step as the subject of the equation. Note that the column vector on the right-hand-side of equation (9) consists of all the known information, including $U_1$, $I_1$ and the system parameters. This crucial step ensures that any item in the column vector on the left-hand-side of equation (9) can be determined.
4. Determine the last two items of the column vector on the left-hand-side of equation (9). That is, obtain $I_n$ and $Z_L I_n$. The item $I_n$ is the load current (i.e. same as $I_{out}$), $Z_L I_n$ is the output voltage ($U_{out}$) of the receiver coil. $I_{out}$ and/or $U_{out}$ can be used in the control loop of FIG. 7 and FIG. 8.
5. The load impedance $Z_L$ can be determined by equation (12) or (16) and the output power $P_{out}$ can be determined by equation (13).

Regarding practical implementation, there are at least two possible approaches:

(A) Using the Magnitudes of $P_{in}$, $U_1$ and $I_1$:

If the instantaneously sampled magnitudes of the envelopes of the $P_{in}$, $U_1$ and $I_1$ waveforms are used for the proposed method, a sampling rate much lower than the operating frequency and a low-cost controller with limited computational power can be used. This is the preferred method as the sampling frequency for the system could be as low as 1 kHz typically. The method involves the following steps:

1) Sample and measure the magnitude of $P_{in}$ and the peak or root-mean-square magnitudes of $U_1$ and $I_1$ at a sampling frequency much lower than the frequency of $U_1$ and $I_1$.
2) Determine the phase angle $\phi$ using equation (11).
3) Use $U_1$ as the reference vector for a rotating frame, then represent $U_1$ and $I_1$ in complex form (either in polar form or Cartesian form).
4) Solve equation (9) for $I_n$ (=$I_{out}$) and $Z_L I_n$ with the $U_1$ and $I_1$ as complex numbers.
5) Determine $U_o$ using equation (14), $Z_L$ using equation (12), $P_{out}$ using equation (13) and $\eta$ (using equation (15)).
6) Then use the calculated $U_{out}$, $I_{out}$, $Z_L$, $P_{out}$, and $\eta$ for an appropriate controller.

(B) Using the Instantaneously Sampled Values of $U_1$ and $I_1$:

If the instantaneously sampled values of the waveforms of $U_1$ and $I_1$ are used for the proposed method, a sampling rate much higher than the operating frequency and a fast computational controller are needed. This is an alternative method and is suitable if very fast samplers and economical fast controllers are available. The alternative method involves the following steps:

1) Sample and measure the instantaneous values of $U_1$ and $I_1$ at a sampling frequency much higher than the frequency of $U_1$ and $I_1$.
2) Solve equation (9) for the instantaneous values of $I_n$(=$I_{out}$) and $Z_L I_n$.
3) Determine $U_o$ using equation (14), $Z_L$ using equation (12), $P_{out}$ using equation (13) and $\eta$ (using equation (15)).
4) Then use the calculated $U_{out}$, $I_{out}$, $Z_L$, $P_{out}$, and $\eta$ for an appropriate controller.

The experimental conditions and calculated self-inductances and mutual-inductances for an 8-coil-domino system are listed in Table 5 to Table 9. The measurement and calculation results are listed in Table 9.

TABLE 5

Self-inductances of each coil for 8-coil-domino system

| | $L_1$ | $L_2$ | $L_3$ | $L_4$ | $L_5$ | $L_6$ | $L_7$ | $L_8$ |
|---|---|---|---|---|---|---|---|---|
| Inductance (H) | 8.204E-05 | 8.204E-05 | 8.204E-05 | 8.204E-05 | 8.204E-05 | 8.204E-05 | 8.204E-05 | 8.204E-05 |

TABLE 6

Mutual-inductances of each pair of coils for 8-coil-domino system

| | $M_{12}$ | $M_{13}$ | $M_{14}$ | $M_{15}$ | $M_{16}$ | $M_{17}$ | $M_{18}$ |
|---|---|---|---|---|---|---|---|
| Inductance (H) | 9.210E−06 | 2.588E−06 | 1.004E−06 | 4.733E−07 | 2.589E−07 | 1.555E−07 | 9.936E−08 |
| | $M_{23}$ | $M_{24}$ | $M_{25}$ | $M_{26}$ | $M_{27}$ | $M_{28}$ | $M_{34}$ |
| Inductance (H) | 8.836E−06 | 2.5544E−06 | 9.887E−07 | 4.734E−07 | 2.584E−07 | 1.537E−07 | 9.048E−06 |
| | $M_{35}$ | $M_{36}$ | $M_{37}$ | $M_{38}$ | $M_{45}$ | $M_{46}$ | $M_{47}$ |
| Inductance (H) | 2.582E−06 | 1.0126E−06 | 4.813E−07 | 2.589E−07 | 8.964E−06 | 2.616E−06 | 1.020E−06 |
| | $M_{48}$ | $M_{56}$ | $M_{57}$ | $M_{58}$ | $M_{67}$ | $M_{68}$ | $M_{78}$ |
| Inductance (H) | 4.772E−07 | 9.212E−06 | 2.658E−06 | 1.015E−06 | 9.158E−06 | 2.5878E−06 | 8.885E−06 |

TABLE 7

Copper resistances of each coil for 8-coil-domino system

| | $R_1$ | $R_2$ | $R_3$ | $R_4$ | $R_5$ | $R_6$ | $R_7$ | $R_8$ |
|---|---|---|---|---|---|---|---|---|
| Resistance (Ohm) | 7.521E−01 | 7.521E−01 | 7.521E−01 | 7.521E−01 | 7.521E−01 | 7.521E−01 | 7.521E−01 | 7.521E−01 |

TABLE 8

Capacitances of each series capacitor for 8-coil-domino system

| | $C_1$ | $C_2$ | $C_3$ | $C_4$ | $C_5$ | $C_6$ | $C_7$ | $C_8$ |
|---|---|---|---|---|---|---|---|---|
| Capacitance (nF) | 1.020 | 1.004 | 1.009 | 9.992 | 9.960 | 1.002 | 1.012 | 1.065 |

TABLE 9

Comparison of calculated impedances and experimental impedances

| Load impedance (Ohm) | Experimental Data from the transmitter | | | | Calculated load impedances (Ohm) | |
|---|---|---|---|---|---|---|
| | Frequency (Hz) | $V_{in}$ (V) | $I_{in}$ (A) | Phase angle (Degree) | Real part | Imaginary part |
| 9.10 | 539751.57 | 1.5070 | 0.0202 | 4.05 | 8.19 | 1.03 |
| 19.30 | 522452.52 | 1.2721 | 0.0315 | −55.93 | 18.58 | −4.71 |
| 19.30 | 535834.47 | 1.0658 | 0.0293 | −9.34 | 18.43 | −4.68 |
| 29.10 | 520632.39 | 1.3734 | 0.0264 | −41.80 | 27.69 | 0.32 |
| 30.00 | 522739.37 | 1.3266 | 0.0285 | −47.74 | 27.10 | −0.46 |
| 39.30 | 521899.22 | 1.3136 | 0.0264 | −34.75 | 36.86 | −2.06 |
| 49.30 | 523702.25 | 1.3132 | 0.0258 | −31.07 | 45.11 | −6.62 |
| 59.20 | 523180.83 | 1.4107 | 0.0233 | −25.78 | 56.64 | −0.68 |
| 69.60 | 523512.07 | 1.4578 | 0.0221 | −22.15 | 66.81 | −3.08 |
| 79.50 | 523707.33 | 1.4909 | 0.0210 | −19.16 | 76.21 | −3.58 |
| 99.60 | 523813.39 | 1.5872 | 0.0189 | −17.07 | 94.99 | −4.01 |
| 119.40 | 523887.33 | 1.6689 | 0.0172 | −14.97 | 116.59 | −3.49 |

C. Output Power Control without Direct Output Information Feedback

The present disclosure can be applied in two different situations. In the first situation the system parameters, i.e., all of the coil resistances, inductance and capacitance as well as mutual inductance between coils, are known. In that situation the measurable input current, input voltage and optionally input power are used to derive the necessary variables ($U_o$, $I_o$, $Z_L$, $P_{out}$ and efficiency) for feeding into the control loop based on equations (5) to (12). Thus, this can be done without using any direct measurement information or feedback from the output (load) side. The variables derived from this method of implementing the disclosure are accurate enough to control the system as if they were measured directly from the outputs.

In the second situation, the system parameters are not known. These unknown parameters are derived from the measurable input current and input voltage only (from the 1st Coil) based on equations (1) to (4) and an intelligent algorithm (such as the Genetic Algorithm) which act to estimate the system parameters, such as the inductance and capacitance values. Once these values are accurately estimated, they are then used for values in the method according to the first situation where these values are known.

(1) Assuming that the System Parameters of the WPTS are Known

If the system parameters of the WPTS are known, the method described in Section B above can be used. The calculated $U_{out}$, $P_L$, $I_n$, and $Z_L$ values now offer information concerning output power control without using directly measured output information. Dynamically updated values of $V_o$, $P_L$, or $I_n$ and $Z_L$ can be used for output power control by controlling either the operating frequency or the input current of the driving coil on the input side.

One example of the control system is illustrated in FIG. 6. Based on the measurable input voltage ($U_{in}$) and input current ($I_{in}$), the method of the present disclosure enables the determination of the information like a variable estimator. The information derived by the variable estimator includes, but is not limited to, the output load impedance ($Z_L$), output voltage ($U_{out}$), output current ($I_{out}$), output power ($P_{out}$) and the system efficiency (η). These variables can be used to fit into any control objective as required in a specific application. It should be noted that the feedback of the estimated efficiency is particularly useful for a wireless power transfer system, because the optimal frequency for maximizing the overall system efficiency can be load dependent. Therefore, the control signals may include both the magnitude of input voltage and/or input current and the frequency.

The main feature of the disclosure is the use of the measurable input variables (namely input voltage and input current) of the first or Transmitter Coil of the wireless power transfer for output load monitoring and output power control, without using any direct measurements from the output load in the Receiver Coil. As such, the wireless power transfer system consists of 2 or more coils.

Figure 7:
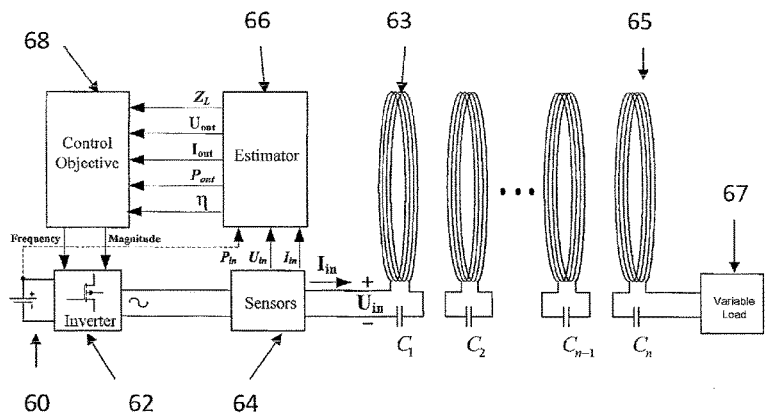
FIG. 7 is a schematic of a control system for a WPTS with known system parameters.

Referring to FIG. 7, the parameters of the wireless power transfer system are presumed to be known, i.e., all coil resistance, inductance and capacitance as well as mutual inductance between coils are given. If the active source is a dc source 60, an inverter 62 with an output filter is used to generate a sinusoidal voltage with controllable frequency and magnitude for driving the first coil (Transmitter Coil 63). Therefore, the input power is provided by energizing the Transmitter Coil and such power will be wirelessly transmitted to the last (Receiver) Coil 65 for powering the load 67. Since according to the disclosure, measurements on the output load are to be eliminated; only the input voltage and the input current can be relied upon for output power control. Note that in the arrangement of FIG. 7 the output load can be connected either in series with the last LC resonator or in parallel across the capacitor of the last LC resonator.

A sensor block 64 in FIG. 7 represents the use of the voltage and current sensors for obtaining such input voltage $U_{in}$ and input current $I_{in}$. The equations (9)-(15) are implemented in an Estimator Block 66. Note that these equations require the input voltage and input current only. Estimator Block 66 may be a microprocessor programmed to execute equations (9)-(15) or some hardware device to perform the same function, such as a programmable gate array or application specific integrated circuit (ASIC).

In the operation of the circuit of FIG. 7, the Estimator 66 solves equation (9) with the (known) measured values of $U_{in}$, Iin in order to obtain $I_2$ to $I_n$ and $Z_L I_{in}$. Then the Estimator generates the variables $Z_L$, $I_o$, $P_o$ and $\eta$ as follows:
 (i) $Z_L$ from equation (12)
 (ii) $P_o$ from equation (13)
 (iii) $U_o$ from equation (14)
 (iv) $I_o = I_n$ obtained already from equation (9)
 (v) $\eta$ from equation (15).
These become the outputs of the Estimator 66.

The first four variables (i)-(iv) are calculated output information, obtained without using any direct output measurements. Together with the energy efficiency, they are calculated continuously at a high sampling rate (usually limited by the speed of the processor) to provide instantaneous output information for control and feedback information. Such calculated values can be fed into any control scheme to meet the specific control objectives of the wireless power transfer system. Based on the chosen control scheme, e.g., control objective 68, the power inverter 62 is operated so that it generates the appropriate sinusoidal voltage at a controllable frequency and magnitude to meet the output power demand of the load 67 according to the control objective.

(2) Assuming that the System Parameters of the WPTS are Unknown

Figure 8:
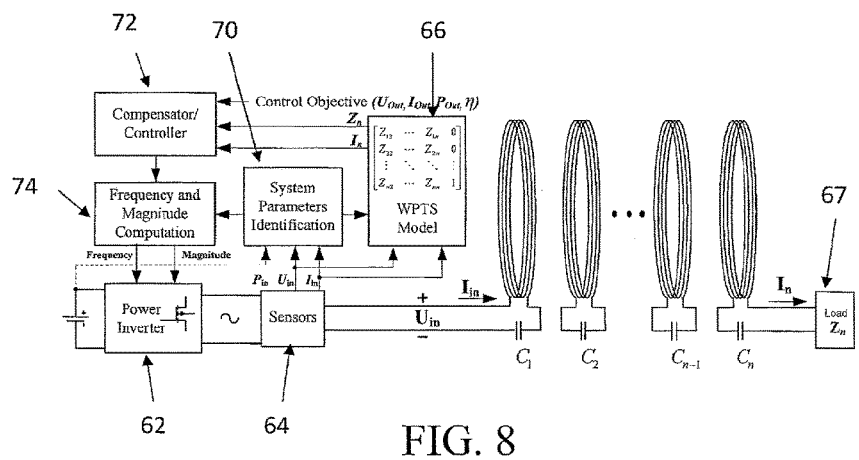
FIG. 8 is a schematic of a control system for a WPTS with unknown system parameters.

If the system parameters are not known, the methods described in both Section A and Section B above are needed and the control block is as shown in FIG. 8. In particular, an extra System Parameters Identification block 70 is included in this control. Here the input voltage and current are also used to determine the system parameters in a real time manner as explained in Section A. As a result, the input voltage and the input current are used to (i) estimate the system parameters dynamically and (ii) provide the control variables for the control system. Thus, unit 70 uses the input voltage $U_{in}$ and current $I_{in}$ to generate the system parameters, i.e., all coil resistance, inductance and capacitance as well as mutual inductance between coils. This is done using equations (1)-(4) and the intelligent algorithm (Genetic Algorithm) to determine the system parameters in the system matrix in equation (1). This method requires only the input voltage and current information.

As an alternative, instead of using the input voltage and current, optionally the input power $P_{in}$ is used. This is shown in dotted line in FIG. 8. If $P_{in}$ is used, the method can be implement easily with a low sampling rate for the envelopes of the input voltage and input current waveforms (without the need for fast sampling of the instantaneous values of the input voltage and current waveforms). This provides a significant savings in computing power.

Once the system parameters are determined, based either on input voltage and current, or input power, the System Parameters Identification unit 70 provides the parameters to the WPTS Model, like the Estimator 66 in FIG. 7, determines the variables $Z_L$, $U_o$, $I_o$, $P_o$ and $\eta$ using equations (5) to (12) as explained above for FIG. 7. These variables are applied to compensator/controller 72, which in part functions in the same way as the control objective 68 in FIG. 7. However, in FIG. 8 the frequency and magnitude compensation are shown as performed in a separate unit 74, whose outputs control the inverter 62.

It should be noted that the output load can be connected either in series with the last LC resonator or in parallel across the capacitor of the last LC resonator.

In summary, FIG. 7 shows a circuit according to the present disclosure which uses the Load Monitoring and Power Control method described in Part-B (for known system parameters). FIG. 8 requires the Parameter Identification Method in Part A and the Load Monitoring & Power Control in Part B, which is for the situation where the system parameters are unknown or are dynamically changing.

The proposed methodology can be applied to a wide range of wireless power applications such as wireless power transfer and load monitoring of medical implants (when the number of coils is reduced to two, i.e. a transmitter coil and a receiver coil), of portable electronic products being charged on a wireless charging pad, and of WPT systems based on the relay resonators or domino-resonator systems (when the number of coils exceeds two). Therefore, the proposed methodology can be applied to any WPT system with 2 or more coils.

Any reference in this specification to "one embodiment," "an embodiment," "exemplary embodiment," etc., means that a particular feature, structure, or characteristic described in connection with the embodiment is included in at least one embodiment of the disclosure. The appearances of such phrases in various places in the specification are not necessarily all referring to the same embodiment. In addition, any elements or limitations of any disclosure or embodiment thereof disclosed herein can be combined with any and/or all other elements or limitations (individually or in any combination) or any other disclosure or embodiment thereof disclosed herein, and all such combinations are contemplated with the scope of the disclosure without limitation thereto.

It should be understood that the examples and embodiments described herein are for illustrative purposes only and that various modifications or changes in light thereof will be suggested to persons skilled in the art and are to be included within the spirit and purview of this application.

While certain exemplary techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that the claimed subject matter not be limited to the particular examples disclosed, but that such claimed subject matter may also include all implementations falling within the scope of the appended claims, and equivalents thereof.

The following is claimed:

1. A method for identifying impedance related parameters in a wireless power transfer (WPT) system including n coils for maximizing an overall WPT system efficiency, the method comprising:

providing a wireless power transfer (WPT) system comprising:

an n number of coils arranged sequentially, wherein a first coil of the n number of coils is a transmitting coil;

at least one capacitor connected to an i-th coil of the n number of coils;

a power source configured to be electrically connected to the first coil of the n number of coils and configured to drive a current through the first coil of the n number of coils;

a plurality of sensors configured to be electrically connected to the first coil of the n number of coils; and a non-transitory computer readable medium configured to receive a signal from a sensor of the plurality of sensors and comprising stored instructions that when executed cause at least one processor to:

sense, by the sensor of the plurality of sensors, input impedances of the WPT system at different respective frequencies $f_k$, (k=1, 2, ... m);

express the measured input impedances at the different respective frequencies as a following first matrix equation:

$$(Z_1, Z_2, \ldots, Z_{m-1}, Z_m) = f\begin{pmatrix} d_{12}, d_{23}, \ldots, d_{(n-2)(n-1)}, d_{(n-1)n}, \\ C_1, C_2, \ldots, C_{n-1}, C_n, \\ R_{load} \end{pmatrix};$$

and determine optimum values of the impedance related parameters based only on a set of the measured input impedances by applying an evolutionary algorithm to solve for the optimum values configured to maximize the overall WPT system efficiency, wherein a capacitance Ci of the capacitor connected to the i-th coil is configured to be adjustable to the determined optimum value of Ci; and wherein a position of at least one coil of the n number of coils is configured to be adjustable to reach a distance equal to the determined optimum value of $d_{ll+1}$, wherein the set of measured input impedances includes an input impedance vector $\vec{Z} = (Z_1, Z_2, \ldots, Z_{m-1}, Z_m)$, each measured input impedance in the vector $Z_k$) being measured at the different respective frequencies $f_k$, (k=1, 2, ... m), and wherein the impedance related parameters included, $d_{ll+1}$ representing the distance between an l-th coil and an l+1 coil (l=1, 2, ... n−1) and $C_i$, representing the capacitance of the capacitor connected to the i-th coil (i=1, 2, ... n).

2. The method for identifying impedance related parameters of claim 1, wherein the input impedance vector is measured experimentally.

3. The method for identifying impedance related parameters of claim 1, wherein n is one of the following values: 3, 4, and 8.

4. The method for identifying impedance related parameters of claim 1, wherein the WPT system is one of the following: a domino WPT system or any other WPT system structure with more than two coils.

5. The method for identifying impedance related parameters of claim 1, wherein a load for the WPT system is connected in series with or in parallel with a capacitor connected to an n-th coil.

6. The method for identifying impedance related parameters of claim 1, wherein the optimum solution solved by the evolutionary algorithm is as follows:

$$J\begin{pmatrix} d_{12}, d_{23}, \ldots, d_{(n-2)(n-1)}, d_{(n-1)n}, \\ C_1, C_2, \ldots, C_{n-1}, C_n, \\ R_{load} \end{pmatrix} = \min\left[\sum_1^m ((|Z_k| + |Z_k^*|)^2 + (\theta_k - \theta_k^*)^2)\right],$$

wherein $R_{load}$ is a predetermined value representing a resistance of a load for the WPT system, and $|Z_k|$ and $\theta_k$ are a magnitude and an angular value, respectively, of the measured input impedance and $|Z^*_k|$ and $\theta^*_k$ are a simulated magnitude and a simulated angular value, respectively, of the input impedance at a respective frequency $f_k$ (k=1, 2, ... m).

7. A method for monitoring a load $Z_L$ in a wireless power transfer (WPT) system including n coils, the method comprising:

sensing only an input voltage $U_1$ and an input current $I_1$ of a transmitter coil of the n coils;

determining a set of measured input impedances based on the sensed input voltage $U_1$ and the sensed input current $I_1$;

identifying impedance related parameters according to the method of any one of claims 1-6;

describing the WPT in terms of the following second matrix equation:

$$\begin{bmatrix} U_1 \\ 0 \\ \vdots \\ 0 \\ 0 \end{bmatrix} = \begin{bmatrix} Z_{11} & Z_{12} & \ldots & Z_{1(n-1)} & Z_{1n} \\ Z_{21} & Z_{22} & \ldots & Z_{2(n-1)} & Z_{2n} \\ \vdots & \vdots & \ddots & \vdots & \vdots \\ Z_{(n-1)1} & Z_{(n-1)2} & \ldots & Z_{(n-1)(n-1)} & Z_{(n-1)n} \\ Z_{n1} & Z_{n2} & \ldots & Z_{n(n-1)} & Z_{nn} + Z_L \end{bmatrix} \begin{bmatrix} I_1 \\ I_2 \\ \vdots \\ I_{n-1} \\ I_n \end{bmatrix};$$

rearranging the second matrix equation into the following third matrix equation:

$$\begin{bmatrix} U_1 - Z_{11}I_1 \\ -Z_{21}I_1 \\ \vdots \\ -Z_{(n-1)1}I_1 \\ -Z_{n1}I_1 \end{bmatrix} = \begin{bmatrix} Z_{12} & \cdots & Z_{1(n-1)} & Z_{1n} & 0 \\ Z_{22} & \cdots & Z_{2(n-1)} & Z_{2n} & 0 \\ \vdots & \vdots & \ddots & \vdots & \vdots \\ Z_{(n-1)2} & \cdots & Z_{(n-1)(n-1)} & Z_{(n-1)n} & 0 \\ Z_{n2} & \cdots & Z_{n(n-1)} & Z_{nn} & 1 \end{bmatrix} \begin{bmatrix} I_2 \\ I_3 \\ \vdots \\ I_n \\ Z_L I_n \end{bmatrix};$$

determining the terms $Z_L I_n$ and $I_n$, and determining the load by using only the sensed input voltage $U_1$, the sensed input current $I_1$, and the identified impedance related parameters.

8. The method for monitoring a load of claim 7, further comprising:

calculating the load $Z_L$ by the equation of $$Z_L = \frac{Z_L I_n}{I_n},$$

wherein $I_n$ represents an output current of the WPT system; and determining the terms $Z_L I_n$ and $I_n$ by using the sensed input voltage $U_1$, the sensed input current $I_1$, and the impedance related parameters.

9. The method for monitoring a load of claim 8, further comprising:

determining the terms $Z_L I_n$ and $I_n$ based on the following equation:

$$\begin{bmatrix} I_2 \\ I_3 \\ \vdots \\ I_n \\ Z_L I_n \end{bmatrix} = \begin{bmatrix} Z_{12} & \cdots & Z_{1(n-1)} & Z_{1n} & 0 \\ Z_{22} & \cdots & Z_{2(n-1)} & Z_{2n} & 0 \\ \vdots & \vdots & \ddots & \vdots & \vdots \\ Z_{(n-1)2} & \cdots & Z_{(n-1)(n-1)} & Z_{(n-1)n} & 0 \\ Z_{n2} & \cdots & Z_{n(n-1)} & Z_{nn}^1 & 1 \end{bmatrix}^{-1} \begin{bmatrix} U_1 - Z_{11}I_1 \\ -Z_{12}I_1 \\ \vdots \\ -Z_{1(n-1)}I_1 \\ -Z_{1n}I_1 \end{bmatrix},$$

wherein $Z_{ij}$ (i=1, 2, ... n, j=1, 2, ... n) is a function of the identified impedance related parameters.

10. The method for monitoring a load of claim 9, further comprising:

determining a power $P_{out}$ of the load $Z_L$, based on the following equation:

$$P_{out} = I_n^2 Re(Z_L).$$

11. The method for monitoring a load of claim 10, further comprising:

determining an efficiency $\eta$ of the WPT system based on one of the following equations:

$$\eta = \frac{P_{out}}{P_{out} + \sum_{x=1}^{n} I_x^2 R_x} \text{ or } \eta = \frac{P_{out}}{U_1 I_1 \cos\varphi},$$

wherein $\varphi$ is an angle between $U_1$ and $I_1$, and wherein $R_x$ is a constant.

12. The method for monitoring a load of claim 11, further comprising:

determining an output voltage $U_o$ of the WPT system based on the following equation:

$$U_o = Z_L I_n.$$

13. A method for controlling output power in a wireless power transfer (WPT) system including n coils for maximizing an overall WPT system efficiency, the method comprising:

providing a wireless power transfer (WPT) system comprising:

an n number of coils arranged sequentially, wherein a first coil of the n number of coils is a transmitting coil;

at least one capacitor connected to an i-th coil of the n number of coils;

a power source configured to be electrically connected to the first coil of the n number of coils and configured to drive a current through the first coil of the n number of coils;

a plurality of sensors configured to be electrically connected to the first coil of the n number of coils; and a non-transitory computer readable medium configured to receive a signal from the a sensor of the plurality of sensors and comprising stored instructions that when executed cause at least one processor to:

(a) sense, by the sensor of the plurality of sensors, an input voltage $U_1$ and an input current $I_1$ of the first coil of the n number of coils;

(b) determine whether impedance related parameters in the WPT system are known, wherein the impedance related parameters include $d_{ll+1}$ representing a distance between an l-th coil and an l+1 coil (l=1, 2, ... n−1) and $C_i$ representing a capacitance of the capacitor connected to the i-th coil (i=1, 2, ... n):

(b.1) if the impedance related parameters in the WPT are known, the method further comprises:

based on the sensed input voltage $U_1$, the sensed input current $I_1$, and the known impedance related parameters, estimating a load $Z_L$ of the WPT system, an output current $I_n$ of the WPT system, a power $P_{out}$ of the load $Z_L$, an output voltage $U_o$ of the WPT system, and an efficiency $\eta$ of the WPT system in the following manner:

calculate the load $Z_L$, by the equation of $$Z_L = \frac{Z_L I_n}{I_n},$$

wherein $I_n$ represents an output current of the WPT system, determine the terms $Z_L I_n$ and $I_n$ based on the following equation:

$$\begin{bmatrix} I_2 \\ I_3 \\ \vdots \\ I_n \\ Z_L I_n \end{bmatrix} = \begin{bmatrix} Z_{12} & \cdots & Z_{1(n-1)} & Z_{1n} & 0 \\ Z_{22} & \cdots & Z_{2(n-1)} & Z_{2n} & 0 \\ \vdots & \vdots & \ddots & \vdots & \vdots \\ Z_{(n-1)2} & \cdots & Z_{(n-1)(n-1)} & Z_{(n-1)n} & 0 \\ Z_{n2} & \cdots & Z_{n(n-1)} & Z_{nn}^1 & 1 \end{bmatrix}^{-1} \begin{bmatrix} U_1 - Z_{11}I_1 \\ -Z_{12}I_1 \\ \vdots \\ -Z_{1(n-1)}I_1 \\ -Z_{1n}I_1 \end{bmatrix},$$

wherein $Z_{ij}$ (i=1, 2, ... n, j=1, 2, ... n) is a function of the identified impedance related parameters, determine the power $P_{out}$ of the load $Z_L$ based on the following equation:

$$P_{out} = I_n^2 Re(Z_L);$$

determine the efficiency η of the WPT system based on one of the following equations:

$$\eta = \frac{P_{out}}{P_{out} + \sum_{x=1}^{n} I_x^2 R_x} \text{ or } \eta = \frac{P_{out}}{U_1 I_1 \cos\varphi},$$

wherein φ is an angle between $U_1$ and $I_1$, and $R_x$ is constant; and
determine the output voltage $U_o$ of the WPT system based on the following equation:

$U_o = Z_L I_n$;

(b.2) if the impedance related parameters are not known, the method further comprises:
determining a set of measured input impedances based on the sensed input voltage $U_1$ and the sensed input current $I_1$,
identifying impedance related parameters in the WPT system based on the sensed input voltage $U_1$, the sensed input current $I_1$, and the identified impedance related parameters, and estimating a load $Z_L$ of the WPT system, an output current of the WPT system $I_n$, power $P_{out}$ of the load $Z_L$, output voltage $U_o$ of the WPT system, and an efficiency η of the WPT system in the following manner:
calculate the load $Z_L$ by the equation of $$Z_L = \frac{Z_L I_n}{I_n},$$

wherein $I_n$ represents an output current of the WPT system,
determine the terms $Z_L I_n$ and $I_n$ based on the following equation:

$$\begin{bmatrix} I_2 \\ I_3 \\ \vdots \\ I_n \\ Z_L I_n \end{bmatrix} = \begin{bmatrix} Z_{12} & \cdots & Z_{1(n-1)} & Z_{1n} & 0 \\ Z_{22} & \cdots & Z_{2(n-1)} & Z_{2n} & 0 \\ \vdots & \vdots & \ddots & \vdots & \vdots \\ Z_{(n-1)2} & \cdots & Z_{(n-1)(n-1)} & Z_{(n-1)n} & 0 \\ Z_{n2} & \cdots & Z_{n(n-1)} & Z_{nn}^1 & 1 \end{bmatrix}^{-1} \begin{bmatrix} U_1 - Z_{11} I_1 \\ -Z_{12} I_1 \\ \vdots \\ -Z_{1(n-1)} I_1 \\ -Z_{1n} I_1 \end{bmatrix},$$

wherein $Z_{ij}$ (i=1, 2, ... n, j=1, 2, ... n) is a function of the identified impedance related parameters,
determine the power $P_{out}$ of the load $Z_L$ based on the following equation:

$P_{out} = I_n^2 Re(Z_L)$;

determine the efficiency η of the WPT system based on one of the following equations:

$$\eta = \frac{P_{out}}{P_{out} + \sum_{x=1}^{n} I_x^2 R_x} \text{ or } \eta = \frac{P_{out}}{U_1 I_1 \cos\varphi},$$

where φ is an angle between $U_1$ and $I_1$, and $R_x$ is a constant; and
determine the output voltage $U_o$ of the WPT system based on the following equation:

$U_o = Z_L I_n$ (c) generate feedback information based on the estimated parameters in either step (b.1) or (b.2); and
(d) control the operations of the first coil based on the generated feedback information to maximize the overall WPT system efficiency.

14. The method of claim 13, wherein identifying impedance related parameters in the WPT system comprises:
determining optimum values of the impedance related parameters based on a set of measured input impedances by applying an evolutionary algorithm to solve for the optimum values,
wherein the set of measured input impedance includes an input impedance vector $\vec{Z} = (Z_1, Z_2, \ldots, Z_{m-1}, Z_m)$, each measured input impedance in the vector $(Z_k)$ measured at different respective frequencies $f_k$, (k=1, 2, ... m),
wherein the impedance related parameters includes $d_{ll+1}$ representing a distance between an l-th coil and an l+1 coil (l=1, 2, ... n−1) and $C_i$ representing a capacitance of a capacitor connected to an i-th coil (i=1, 2, ... n),
wherein a capacitance $C_i$ of the capacitor connected to an i-th coil is configured to be adjustable to the determined optimum value of $C_i$; and
wherein a position of at least one coil of the n number of coils is configured to be adjustable to reach a distance equal to the determined optimum value of $d_{ll+1}$.

15. The method of claim 14, wherein the input impedance vector is measured experimentally.

16. The method of claim 14, wherein n is one of the following values: 3, 4, and 8.

17. The method of claim 14, wherein the WPT system is one of the following: a domino WPT system or any other WPT system with more than two coils.

18. The method of claim 14, wherein a load for the WPT system is connected in series with or in parallel with a capacitor connected to an n-th coil.

19. The method of claim 14, wherein an optimum solution is solved by the following evolutionary algorithm:

$$J\begin{pmatrix} d_{12}, d_{23}, \ldots, d_{(n-2)(n-1)}, d_{(n-1)n}, \\ C_1, C_2, \ldots, C_{n-1}, C_n, \\ R_{load} \end{pmatrix} = \min\left[\sum_1^m ((|Z_k| + |Z_k^*|)^2 + (\theta_k - \theta_k^*)^2)\right],$$

wherein $R_{load}$ is a predetermined value representing the resistance of a load for the WPT system,
and $|Z_k|$ and $\theta_k$ are a magnitude and an angular value, respectively, of the measured input impedance and $|Z^*_k|$ and $\theta^*_k$ are a simulated magnitude and a simulated angular value, respectively, of the measured input impedance at a respective frequency $f_k$(k=1, 2, ... m).

* * * * *

UNITED STATES PATENT AND TRADEMARK OFFICE
CERTIFICATE OF CORRECTION

PATENT NO. : 10,224,751 B2
APPLICATION NO. : 14/910560
DATED : March 5, 2019
INVENTOR(S) : Shu Yuen Hui et al.

Page 1 of 1

It is certified that error appears in the above-identified patent and that said Letters Patent is hereby corrected as shown below:

In the Specification

Column 12,
Line 26, "$I_n$ $(=L_{out})$" should read --$I_n$ $(=I_{out})$--.

Column 15,
Line 41, "$Z_L$, $I_o$, $P_o$, and $\eta$" should read --$Z_L$, $U_o$, $I_o$, $P_o$ and $\eta$--.

In the Claims

Column 20,
Claim 13, Line 21, "from the a sensor" should read --from a sensor--.

Column 22,
Claim 14, Line 22, "at- different" should read --at different--.

Signed and Sealed this
Thirtieth Day of July, 2019

Andrei Iancu
*Director of the United States Patent and Trademark Office*